United States Patent [19]

Oneto et al.

[11] 4,306,997

[45] Dec. 22, 1981

[54] FOAM BATH COMPOSITIONS CONTAINING ANIONIC DETERGENT AND MONOGLYCERIDE

[75] Inventors: Francis E. J. Oneto, Clichy-sous-Bois; Andre J. E. Benzoni, Livry-Gargan; Jacques L. Poret, Mitry-Mory; Fernand B. Simon, Margency, all of France

[73] Assignee: Lever Brothers Company, New York, N.Y.

[21] Appl. No.: 173,566

[22] Filed: Jul. 30, 1980

Related U.S. Application Data

[63] Continuation of Ser. No. 758,777, Jan. 12, 1977, abandoned.

[30] Foreign Application Priority Data

Jan. 16, 1976 [GB] United Kingdom ............... 1792/76

[51] Int. Cl.$^3$ ............... A61K 7/50; C11D 1/29; C11D 3/46; C11D 17/08
[52] U.S. Cl. ............... 252/541; 252/89.1; 252/173; 252/174.21; 252/545; 252/550; 252/551; 252/DIG. 5; 252/DIG. 13; 252/DIG. 14; 424/70; 424/312; 424/365
[58] Field of Search ............... 252/550, 551, 546, 89.1, 252/174.21, DIG. 5, DIG. 13, DIG. 14, 173, 541, 545; 424/70, 365, 312

[56] References Cited

U.S. PATENT DOCUMENTS

| | | | |
|---|---|---|---|
| 2,183,853 | 12/1939 | Haussmann et al. | 260/404 |
| 2,398,296 | 4/1946 | Epstein et al. | 424/365 X |
| 3,424,849 | 1/1969 | Conklin et al. | 424/365 |
| 3,703,481 | 11/1972 | Barker et al. | 252/DIG. 5 X |
| 3,723,360 | 3/1973 | Hewitt | 252/DIG. 13 X |
| 3,798,179 | 3/1974 | Hellyer | 252/550 X |
| 3,819,538 | 6/1974 | Little et al. | 252/527 |
| 3,829,563 | 8/1974 | Barry et al. | 424/70 |
| 3,943,234 | 3/1976 | Roggenkamp | 252/DIG. 5 X |
| 4,130,497 | 12/1978 | Oneto et al. | 252/DIG. 5 X |
| 4,148,762 | 4/1979 | Koch et al. | 252/DIG. 5 X |

FOREIGN PATENT DOCUMENTS

| | | | |
|---|---|---|---|
| 831483 | 1/1970 | Canada | 424/171 |
| Ad.96188 | 5/1972 | France | 252/DIG. 13 X |
| 1169496 | 11/1969 | United Kingdom . | |
| 1174672 | 12/1969 | United Kingdom | 424/312 |
| 1333475 | 10/1973 | United Kingdom | 424/171 |

OTHER PUBLICATIONS

Lesser, "Shampoos", *Soap and Sanitary Chemicals,* Jan. 1951, pp. 38-41, 61, 71, 115, 117 & 119.

*Primary Examiner*—Dennis L. Albrecht
*Attorney, Agent, or Firm*—Irving N. Feit; James J. Farrell; Melvin H. Kurtz

[57] ABSTRACT

A single liquid phase detergent composition, such as a foam bath product, contains an alkyl monoglyceride as a skin benefit agent, an anionic detergent and water. In use, when diluted in water, the composition is capable of producing and maintaining a substantial head of foam and is capable of depositing on the skin, after immersion, a noticeable amount of the alkyl monoglyceride.

12 Claims, No Drawings

FOAM BATH COMPOSITIONS CONTAINING ANIONIC DETERGENT AND MONOGLYCERIDE

This application is a continuation of application Ser. No. 758,777, filed Jan. 12, 1977, now abandoned.

The invention relates to foam bath compositions adapted to be added to bath water or for use when showering, which can on dilution with water produce a stable foam and also provide a film of a skin benefit agent on the skin which is retained after emerging from the bath or shower.

Some bath products for addition to bath water leave a film of oil on the skin. Generally, these products comprise an oil which tends to float on the surface of the bath water, which can interfere with the lathering of soap and which may leave a deposit of scum around the bath above the waterline which is inconvenient to remove after the bath water has drained away.

Some other bath products comprise a foam-producing surface active agent which when added to bath water with agitation can produce copious foam; such products generally reduce the problem of scum formation.

Whereas it is possible to prepare bath products containing both oil and foaming detergents, it is generally believed that foaming is inhibited by the presence of the oil and that therefore these two components of the product are non-compatible. It has also been recognized that products of this type containing a detergent and an oil will tend to separate on standing so that the bath product will generally consist of two liquid phases which will require mixing thoroughly before dispensing in the bath water in order to ensure addition of the correct proportion of each phase.

Contrary to expectation, we have now discovered that it is possible to employ a special detergent and a special oily skin benefit ingredient which in admixture provide a single liquid phase product which does not partition on standing and which can be transparent. The product is adapted for addition to bath water to yield a copious foam which is stable in the presence of the oily skin benefit ingredient, the product also providing a film of the skin benefit ingredient which is retained on the skin after emerging from the bath.

Accordingly, the invention provides a single liquid phase detergent composition comprising
(i) from 1 to 50% by weight of a $C_8$ to $C_{14}$ alkyl monoglyceride containing an average of from 0 to 3 moles of ethylene oxide;
(ii) from 5 to 50% by weight of an anionic detergent selected from
  (a) a sodium, potassium, magnesium, ammonium or a substituted amine, $C_8$ to $C_{18}$ fatty alcohol sulphate containing an average of from 0 to 4 moles of ethylene oxide,
  (b) an alkyl or alkylaryl substituted ethoxylated oxacarboxylic acid or a sodium or an amine salt thereof having the empirical formula:

$$R.(OCH_2CH_2)_n.OCH_2COOX$$

where
  R is $C_8$ to $C_{18}$ alkyl or $C_6$ to $C_{12}$ alkyl phenyl;
  n has an average value of from 1 to 15; and
  X is hydrogen, sodium or an amine residue, and
  (c) mixtures thereof; and
(iii) water.

The $C_8$ to $C_{14}$ alkyl monoglyceride which forms the oily skin benefit ingredient of the composition is preferably monolaurin. Monocaprylin, monocaprin, monomyristin and the corresponding ethoxylated forms of these four monoglycerides, each preferably containing an average of up to 3 moles of ethylene oxide, are skin benefit ingredients which can be used in place of monolaurin. It is also possible to use a mixture of two or more of these monoglycerides.

It is furthermore possible to employ unrefined materials, such as that derived from the partial saponification of fats and oils, which are rich in $C_8$ to $C_{14}$ alkyl monoglycerides. In this case, however, it is preferable that the unrefined material should contain not less than 90% by weight of the monoglycerides and not more than 10% of diglycerides, as the latter will generally interfere with the formation and maintenance of a satisfactory foam when the composition is employed in the bath.

The reason for selecting monoglycerides which contain an average of from 0 to 3 moles of ethylene oxide is that they are less soluble in water than those containing more than 3 moles of ethylene oxide. In consequence, these less soluble monoglycerides show a greater tendancy to be deposited on the skin than do the more soluble forms. This can be demonstrated by the radiotracer technique referred to later in this specification which measures total monoglyceride deposited on, absorbed by and otherwise retained by the skin after immersion in bath water containing the composition according to the invention.

Although the quantity of the alkyl monoglyceride containing an average of from 0 to 3 moles of ethylene oxide employed forms from 1 to 50% by weight, it is preferable to use from 2 to 10%, most preferably from 4 to 6% by weight of the detergent composition.

Use of less than 1% by weight of the monoglyceride is unlikely in use to provide the bather with a noticeable skin benefit, whereas use of more than 50% by weight can cause the product to partition on storage and can tend to depress the ability of the composition to produce a copious foam.

The special detergent for incorporation in the composition according to the invention is selected from an anionic detergent comprising a sodium, potassium, magnesium, ammonium or a substituted amine $C_8$ to $C_{18}$ fatty alcohol sulphate containing an average of from 0 to 4 moles of ethylene oxide, and an alkyl or alkylaryl substituted ethoxylated oxacarboxylic acid or a sodium or an amine salt thereof having the empirical formula:

$$R.(OCH_2CH_2)_n.OCH_2COOX$$

where
R is $C_8$ to $C_{18}$ alkyl or $C_6$ to $C_{12}$ alkyl phenyl;
n has an average value of from 1 to 15; and
x is hydrogen, sodium or an amine residue, and mixtures thereof.

Preferred examples of the $C_8$ to $C_{18}$ fatty alcohol sulphate are sodium lauryl sulphate, sodium lauryl ether sulphate, magnesium lauryl sulphate, mono-, di- or triethanolamine salts of lauryl sulphate or lauryl ether sulphate having an average of from 2 to 3 moles of ethylene oxide and amine salts of lauryl sulphate and lauryl ether sulphate such as the diethylamine and monobutylethanolamine salts of lauryl ether sulphate.

Preferred examples of the ethoxylated oxacarboxylic acid or salt are those having an average of 4 to 5 moles ethylene oxide in which the salt is an amine of lauryl (poly-1-oxapropene) oxaethane carboxylic acid, the amine being 3-methoxy-n-propylamine, propylamine, dibutylamine, isopropylamine, or monobutylethanolamine. The corresponding sodium salt of lauryl (poly-1-oxapropene) oxaethane carboxylic acid is a further preferred example.

The anionic detergent employed functions to provide a copious foam when the composition is diluted with agitation in bath water. The detergent also functions to maintain the alkyl monoglyceride in solution in the composition before dilution by addition to bath water or before use when showering. By this means, the composition does not partition into two or more liquid phases on standing at the normal temperature of storage which is usually from 5° to 20° C.

Although the quantity of the anionic detergent employed is by weight from 5 to 50%, it is preferable to use from 10 to 25%. These values refer to the weight of active detergent present.

Use of less than 5% by weight of the anionic detergent is likely to be insufficient to maintain the monoglyceride in solution and is also unlikely to produce a copious foam when the composition is diluted with agitation in bath water. On the other hand, use of more than 50% by weight of anionic detergent in the composition is unlikely further to improve the solution of the monoglyceride in the composition and can also function to produce a foam which is too copious, a property which might persuade the user to employ less of the composition in the bath water than is necessary to provide a noticeable skin benefit from retention of the monoglyceride on the skin. Furthermore, an excessive concentration of the anionic detergent even after dilution in use might lead to irritation or other skin damage.

The amount of water which is incorporated in the composition should be sufficient to ensure that the composition maintains its single liquid phase character. Normally, the composition will comprise from 20 to 90% by weight of water, including that which can be provided in the detergent ingredient as supplied by the manufacturer.

In addition to the oily skin benefit ingredient and the anionic detergent and water, it is also possible to incorporate in the composition other ingredients such as thickeners, foam boosters, foam stabilizers, coloring matter, perfumes and preservatives, the amounts of such additional optional material being similar to those which are usually employed in bath or shower products.

When required for use, the composition can be diluted as required by the user, but as a guide, we have found that addition of 30 g of the composition with agitation to a total of 100 liters of bath water, giving a dilution of the composition of about 0.3 g/l, is ideal for producing a copious foam and for depositing a clearly noticeable film of the oily skin benefit agent on the skin of the bather. As a further guide, it is apparent that a dilution of the composition in water of from 0.1 to 0.5 g/l is preferred.

It should be explained that reference herein to the ability of detergent compositions according to the invention to produce a "copious foam" when mixed with bath water means that they satisfy a laboratory test for foam production which can be carried out under standard conditions as follows.

Test for the Determination of the Foaming Power of a Detergent Composition

A 3 g sample of a detergent composition to be tested is placed in a graduated glass tank of rectangular cross section 200 mm wide × 600 mm long × 40 mm deep. The tank is fitted with an overhead sparger tube resting on the top edges of the tank, the sparger being drilled with 24 holes each 0.9 mm in diameter and spaced 16 mm apart along the length of the tank.

At the commencement of the test, water at a temperature of 37° C. and having a degree of hardness of 30° (French) is admitted to the tank via the sparger holes at a flow rate of 4.4 l/min via a standard metering pump until the total volume of water admitted is 10 liters. The foam height in mm above the water level is then read immediately and it is this figure which is used to assess the foaming power of the test sample of the detergent composition.

A sample which is capable of producing under these conditions a foam height of 20 mm or more is said to be capable of producing a copious foam.

Preferred detergent compositions according to the invention are those which are capable of producing a foam height of at least 40 mm and the best compositions are capable of producing a foam height of at least 50 mm.

Reference has also been made to the deposition on and retention by the skin of the skin benefit ingredient of the detergent composition. This is usually discernible as a pleasantly smooth or supple feeling which is imparted to the skin after having been immersed in the foaming bath water and after removal of surplus water, for example with a towel. It is appreciated however that the reaction between individuals will vary because of the subjective nature of their appreciation of the deposited skin benefit ingredient. Accordingly, a test for measuring objectively the amount of skin benefit ingredient which is actually retained by the skin has been devised. In this test, to be described later, a conventional radiochemical technique is employed in which adsorption of labelled monoglyceride on excised human skin is measured, and by this means it is possible to judge the ability of the detergent composition in use to deposit the skin benefit ingredient on the skin.

Although, as has been indicated, it is difficult to assay subjectively the amount of monoglyceride deposited on and retained by the skin, a clinical method for comparing the effect of detergent compositions according to the invention with those of other detergent compositions, has been devised. This method, which employs a panel of trained assessors who score the skin condition of a group of persons before and after treatment with test and control compositions, is described in detail later.

The detergent compositions according to the invention are preferably transparent and are usually formulated for use as foam bath products, but as we have indicated, they can also be formulated to provide products for use when showering, such as shower gels. As further alternatives the detergent composition can be shampoo products, dishwashing products, fabric washing products, especially for improving the texture of wool and silk products.

The invention also provides a process for the production of a single liquid phase detergent composition which is characterized by the steps of:

(i) diluting with water an anionic detergent selected from
  (a) a sodium, potassium, magnesium, ammonium or a substituted amine, $C_8$ to $C_{18}$ fatty alcohol sulphate containing an average of from 0 to 4 moles of ethylene oxide,
  (b) an alkyl or alkylaryl substituted ethoxylated oxacarboxylic acid or a sodium or an amine salt thereof having the empirical formula:

$$R.(OCH_2CH_2)_n.OCH_2COOX$$

where
  R is $C_8$ to $C_{18}$ alkyl or $C_6$ to $C_{12}$ alkyl phenyl;
  n has an average value of from 1 to 18; and
  X is hydrogen sodium or an amine residue, and
  (c) mixtures thereof; and
(ii) blending the diluted aqueous anionic detergent so formed with a $C_8$ to $C_{14}$ alkyl monoglyceride containing an average of from 0 to 3 moles of ethylene oxide; the amount of the anionic detergent before dilution forming from 5 to 50% by weight of the composition and the amount of the monoglyceride forming from 1 to 50% by weight of the composition, the composition so produced forming a single liquid phase.

The invention is illustrated by the following examples.

EXAMPLE 1

A skin benefit foam bath composition was prepared by mixing together the following ingredients:

| | % w/w |
|---|---|
| AKYPOSAL 100 LFS (Diethylamine and monobutylethanolamine salt of lauryl ether sulphate ($C_{12}:C_{14}$ = 70:30, 2,2EO) 100% AD) | 20 |
| Monolaurin | 5 |
| GENAGEN CA 050 (Ethoxylated (5EO) copra monoethanolamide) | 3 |
| Perfume, color, water to | 100 |

The foaming power height according to the test described herein was 55 mm.

EXPERIMENT

An experiment was conducted using the skin benefit foam bath composition of Example 1 to illustrate the method employed for measuring the deposition of monoglyceride on the skin after treatment with the detergent composition after appropriate dilution.

A 10 cm$^2$ piece of dried human skin (stratum corneum) weighing 10 mg was placed in a beaker containing 10 ml of diluted detergent composition (0.25 g/l) itself containing 5% by weight, expressed in terms of the detergent composition, monolaurin $^3$H.

A radiotracer method was employed to determine the amount of labelled monoglyceride initially present in the diluted detergent composition. After 24 hours, the skin was removed, rinsed with water, incinerated and the amount of tritiated monoglyceride retained by the skin was determined by the liquid scintillation technique.

The results showed that 0.6 μm of the monoglyceride were retained by per gram of stratum corneum.

EXAMPLE 2

A skin benefit foam bath having similar properties to that described in Example 1 can be prepared by mixing together the following ingredients:

| | % w/w |
|---|---|
| TEXAPON T42 (Triethanolamine salt of lauryl sulphate) | 48 |
| Monocaprin | 5 |
| GENAGEN CA 050 | 2 |
| Perfume, color, water to | 100 |

EXAMPLE 3

A skin benefit foam bath composition was prepared by mixing together the following ingredients:

| | % w/w |
|---|---|
| GENAPOL CRO [sodium lauryl ether sulphate (28% AD)] | 54 |
| Monolaurin | 5 |
| A mixture of ethoxylated (1 to 3 EO) $C_8$-$C_{12}$ glycerides | 6 |
| CARBITOL (diethylene glycol mono ethyl ether) | 3 |
| Perfume, color, water to | 100 |

The ethoxylated $C_8$-$C_{12}$ glycerides and the CARBITOL together aid solubilization of monolaurin in this composition.

The foaming power height according to the test described herein was 60 mm.

The amount of monoglyceride deposited on skin from this skin benefit foam bath composition, using the experimental radiotracer technique as described herein, was 0.4 μM/g.

EXAMPLE 4

A skin benefit foam bath having similar properties to that described in Example 3 was prepared by mixing together the following ingredients:

| | % w/w |
|---|---|
| GENAPOL CRO | 54 |
| Monolaurin | 5 |
| EMKANOL MDG (diethylene glycol mono ethyl ether) | 6 |
| GENAGEN CA 050 | 2 |
| Perfume, color, water to | 100 |

The foaming power height according to the test described herein was 55 mm.

The amount of monoglyceride deposited on the skin from this skin benefit foam bath composition, using the experimental radiotracer technique as described herein, was 0.53 μM/g.

EXAMPLE 5

Example 4 can be repeated by replacing EMKANOL MDG with an equivalent amount of glycerine.

EXAMPLE 6

A skin benefit foam bath having similar properties to that described in Examples 3,4 and 5 can be prepared by mixing together the following ingredients:

|  | % w/w |
|---|---|
| TEXAPON T42 | 48 |
| A mixture of ethoxylated (1 to 3 EO) $C_8$-$C_{12}$ glycerides | 5 |
| GENAGEN CA 050 | 3 |
| Perfume, color, water to | 100 |

EXAMPLE 7

A skin benefit foam bath composition was prepared by mixing together the following ingredients:

|  | % w/w |
|---|---|
| TEXAPON T42 | 24 |
| AKYPOSAL 100 LFS | 10 |
| Monolaurin | 5 |
| GENAGEN CA 050 | 3 |
| Perfume, color, water to | 100 |

The foaming power height according to the test described herein was 47 mm.

The amount of monoglyceride deposited on skin from this skin benefit foam bath composition, using the experimental radiotracer technique as described herein, was 0.9 $\mu M/g$.

EXPERIMENT

The skin benefit foam bath composition of Example 7 was compared with a commercially available foam bath product as a control, the comparison being on the basis of subjective assessments by a panel of trained assessors who judged the skin condition of a group of subjects before and after treatment with each product.

The experiment was carried out as follows.

A group of 15 subjects were asked to immerse the forearm and hand of each arm (according to a statistical design) in a trough containing either the test or the control product diluted to a concentration of 0.25 g/l at a temperature of 35°-38° C. Immersion took place for 15 minutes daily, five days a week for four weeks.

The skin of the hands and elbows of each subject was assessed at the beginning and at the end of the experiment, the appearance and feel of the skin being scored according to the following hedonic scale:
0: skin nice and soft
1: skin slightly dry
2: skin dry
3: skin very dry
4: skin very dry, slightly cornified
5: skin very dry, cornified The test composition used was as described above under Example 7.

The control composition used as a commecially available foam bath product which had the following formulation:

|  | % w/w |
|---|---|
| Sodium lauryl ether sulphate (3EO) 28% AD | 60 |
| Foam stabilizer | 2 |
| AUBYGUM SD (depolymerized seaweed extracts) | 0.9 |
| Perfume, color, water to | 100 |

The results of the subjective assessment were as follows:

|  | CONTROL | TEST (EXAMPLE 7) |
|---|---|---|
| Δmean score (Duncan test) | −0.40 | +0.19 |
| General comment | slight deterioration in skin condition | Slight improvement in skin condition |

The results were subjected to a statistical analysis of variance as summarized in the Table below.

TABLE 1

| | Analysis of variance | | | | |
|---|---|---|---|---|---|
|  | Degrees of freedom | Sum of squares | Mean square | F value | |
| Treatments | 1 | 7.93 | 7.93 | 6.78 | P<0.05 |
| Assessors | 1 | 0.39 | 0.39 | 0.33 | Not significant |
| Area (hand versus elbow) | 1 | 5.26 | 5.26 | 4.50 | P<0.05 |
| Subjects | 22 | 40.61 | 1.85 | 1.58 | Not significant |
| Error | 66 | 77.42 | 1.17 | | |

The conclusions of this analysis show that
(i) the test and control treatments were significantly different at P<0.05;
(ii) there was no significant difference between the scores of the two assessors;
(iii) the scores for the skin of the elbow was significantly different from the score for the skin of the hand at P<0.05: this difference was thought to be due to the fact that the hands were washed more frequently during the test period than were the corresponding elbows. Hence, the results for the skin of the hand were discounted;
(iv) there was no significant difference between the scores derived from the 23 subjects, thus indicating that the panel was suitably chosen.

In conclusion, it was evident that the Test sample result was statistically significantly better than that of the Control, indicating the skin benefit effect of the monoglyceride:

EXAMPLE 8

A skin benefit foam bath having similar properties to that described in Example 7 can be prepared by mixing together the following ingredients:

|  | % w/w |
|---|---|
| AKYPOSAL 100 LFS | 20 |
| Monocaprylin | 5 |
| GENAGEN CA 050 | 3 |
| Perfume, color, water to | 100 |

EXAMPLE 9

A skin benefit foam bath composition was prepared by mixing together the following ingredients:

|  | % w/w |
|---|---|
| Lauryl (poly-1-oxapropane) oxaethane carboxylic monobutylethanolamine salt (450E) (90% AD) | 20 |
| Monolaurin | 5 |
| GENAGEN CA 050 | 3 |

| | % w/w |
|---|---|
| Perfume, color, water to | 100 |

The foaming power height according to the test described herein was 25 mm.

The compositions of Examples 1 to 9 each consist of a single transparent liquid phase which can be diluted to a concentration of 0.25 g composition per liter of bath water to provide with agitation a copious foam and to deposit on the skin of the bather a noticeable slightly oily feel.

EXAMPLE 10

A shower gel product was prepared by mixing together the following ingredients:

| | % w/w |
|---|---|
| TEXAPON T42 | 40 |
| AKYPOSAL 100 LFS | 10 |
| Monolaurin | 8 |
| Perfume, color, water to | 100 |

EXAMPLE 11

A shower gel product was prepared by mixing together the following ingredients:

| | % w/w |
|---|---|
| Magnesium lauryl sulphate | 15 |
| Monolaurin | 5 |
| Perfume, color, water to | 100 |

The selection of magnesium lauryl sulphate as the anionic detergent gives the composition a particularly mild property in that delicate skins are less likely to suffer irritation than when more conventional anionic detergents are used.

What is claimed is:

1. A single liquid phase detergent composition capable of producing a copious foam when mixed with water, said composition comprising
   (i) from 1 to 50% by weight of a $C_8$ to $C_{14}$ alkyl monoglyceride containing an average of from 0 to 3 moles of ethylene oxide;
   (ii) from 5 to 50% by weight of an anionic detergent selected from
      (a) a sodium, potassium, magnesium, ammonium or a substituted amine, $C_8$ to $C_{18}$ fatty alcohol sulphate containing an average of from 0 to 4 moles of ethylene oxide; and
      (b) an alkyl or alkylaryl substituted ethoxylated oxacarboxylic acid or a sodium or an amine salt thereof having the empirical formula:

$R.(OCH_2CH_2)_n.OCH_2COOX$ where R is $C_8$ to $C_{18}$ alkyl or $C_6$ to $C_{12}$ alkyl phenol; n has an average value of from 1 to 15; and X is hydrogen, sodium, or an amine residue; and
      (c) mixtures thereof; and
   (iii) from 20 to 90% by weight water.

2. A composition according to claim 1, wherein the monoglyceride is selected from monocaprin, monocaprylin, monolaurin and monomyristin or mixtures thereof.

3. A composition according to claim 1, wherein the monoglyceride is ethoxylated.

4. A composition according to claim 1, wherein the monoglyceride forms from 2 to 10% by weight of the composition.

5. A composition according to claim 1, wherein the anionic detergent comprises a substituted amine salt of lauryl sulphate or lauryl ether sulphate having an average of 2 to 3 moles of ethylene oxide.

6. A composition according to claim 1, wherein the anionic detergent comprises sodium lauryl sulphate or sodium lauryl ether sulphate.

7. A composition according to claim 1, wherein the anionic detergent comprises magnesium lauryl sulphate.

8. A composition according to claim 1, wherein the anionic detergent comprises an amine of lauryl (poly-1-oxapropene) oxaethane carboxylic acid, the amine being selected from 3-methoxy-n-propylamine, propylamine, dibutylamine, isopropylamine or monobutylethanolamine.

9. A composition according to claim 1, wherein the anionic detergent forms from 10 to 25% by weight of the composition expressed in terms of the active detergent present.

10. A composition according to claim 1, which is a liquid foam bath composition.

11. A composition according to claim 1, which is a shower gel composition.

12. A composition according to claim 1 wherein said anionic detergent is selected from an alkyl or alkylaryl substituted ethoxylated oxacarboxylic acid or a sodium or an amine salt thereof having the empirical formula:

$R.(OCH_2CH_2)_n.OCH_2COOX$ where
R is $C_8$ to $C_{18}$ alkyl or $C_6$ to $C_{12}$ alkyl phenol;
n has an average value of from 1 to 15; and
X is hydrogen, sodium, or an amine residue; and mixtures thereof.

* * * * *